United States Patent [19]

Fuhge et al.

[11] Patent Number: 4,650,678

[45] Date of Patent: Mar. 17, 1987

[54] READILY DISSOLVABLE LYOPHILIZED FIBRINOGEN FORMULATION

[75] Inventors: Peter Fuhge, Lahntal; Norbert Heimburger, Marburg; Hans-Arnold Stöhr, Wetter; Wolfgang Burk, Gladenbach-Mornshausen, all of Fed. Rep. of Germany

[73] Assignee: Behringwerke Aktiengesellschaft, Fed. Rep. of Germany

[21] Appl. No.: 639,617

[22] Filed: Aug. 10, 1984

Related U.S. Application Data

[63] Continuation-in-part of Ser. No. 463,289, Feb. 2, 1983, abandoned.

[30] Foreign Application Priority Data

Feb. 4, 1982 [DE] Fed. Rep. of Germany ....... 3203775

[51] Int. Cl.[4] .................. A61K 35/14; A61K 31/155; A61K 31/17; A61K 31/195
[52] U.S. Cl. ...................................... 424/101; 514/2; 514/565; 514/588

[58] Field of Search ...................... 424/177, 101; 514/2

[56] References Cited

U.S. PATENT DOCUMENTS

| | | | |
|---|---|---|---|
| 4,294,753 | 10/1981 | Urist | 424/177 |
| 4,298,598 | 11/1981 | Schwarz et al. | 424/101 |
| 4,362,567 | 12/1982 | Schwarz et al. | 424/101 |
| 4,377,572 | 3/1983 | Schwarz et al. | 424/101 |
| 4,414,976 | 11/1983 | Schwarz et al. | 128/334 |
| 4,440,679 | 4/1984 | Fernandes | 424/101 |

*Primary Examiner*—Donald B. Moyer
*Assistant Examiner*—Jacqueline M. Stone
*Attorney, Agent, or Firm*—Finnegan, Henderson, Farabow, Garrett & Dunner

[57] ABSTRACT

A solid fibrinogen formulation is described, which formulation contains, in addition to fibrinogen, a substance containing the urea or guanidine radical, and a process for its preparation. This formulation is used for the preparation of a fibrinogen solution which is suitable as an adhesive for human and animal tissue and as a fibrinogen concentrate for intravenous administration.

5 Claims, No Drawings

READILY DISSOLVABLE LYOPHILIZED FIBRINOGEN FORMULATION

This application is a continuation-in-part of application Ser. No. 463,289, filed 2/2/83, now abandoned.

The invention relates to a solid fibrinogen formulation and to a process for its preparation. This formulation can be used for the preparation of a fibrinogen solution which is suitable as an adhesive for human and animal tissue and as a solution for intravenous administration.

It is known that it is only possible slowly, at elevated temperature and only in low concentration to bring into solution again lyophilized fibrinogen and lyophilizates of plasma proteins containing a high proportion of fibrinogen.

Fibrinogen has been used for some time as a physiological adhesive for taking care of injuries to parenchymal organs, bones or vessels. For this indication, it is necessary to dissolve the fibrinogen in as high a concentration as possible, since the adhesive action is a function of the fibrinogen concentration. Since fibrinogen solutions having the necessary content of 8 to 10% of coagulable fibrinogen can only be prepared from fibrinogen lyophilizates with difficulty, deep-frozen fibrinogen-containing so-called cryoprecipitate is used for tissue adhesion.

However, this use of deep-frozen cryoprecipitate is associated with disadvantages, since preparations of this type are unstable and must be kept at a temperature below $-20°$ C. until used.

A solid fibrinogen formulation, which could be dissolved to give a fibrinogen solution containing at least 7 g/100 ml, would thus be a great advantage.

Furthermore, a fibrinogen solution of this type at a lower concentration of about 2% of fibrinogen can be employed as an intravenous preparation for situations involving acute use of fibrinogen in patients with various diseases. At present, fibrinogen concentrates are employed for this purpose, which are prepared from the cryoprecipitate and contain various additional plasma proteins. In contrast, pure fibrinogen is not employed nowadays.

Thus, the present invention has the object of making available a formulation based on pure fibrinogen which, because of its properties, can be employed both as a fibrin adhesive and as a fibrinogen concentrate for intravenous administration to humans and which has good solubility.

A fibrinogen lyophilizate, which is said to be suitable as a tissue adhesive, has been disclosed in German Offenlegungsschrift No. 3,002,934. This lyophilizate is also a cryoprecipitate, which accordingly contains not only fibrinogen and factor XIII, but also plasminogen, albumin and other plasma constituents. An inhibitor of plasminogen activator is added to stabilize the lyophilizate and the reconstituted solution. This lyophilizate is sparingly, and only at elevated temperature ($37°$ C.), soluble. After reconstitution, the product is stable for a maximum of 4 hours at room temperature.

A lyophilized fibrinogen formulation has now been found, which formulation need not contain either an inhibitor of plasminogen activator or albumin to stabilize it and which is suitable for the preparation of highly concentrated fibrinogen solutions (about 8%) even at room temperature. It is unnecessary to employ cryoprecipitate as the starting point, since it is also possible to employ pure fibrinogen as the starting product.

This was made possible by the surprising finding that the solubility of fibrinogen lyophilizates is increased and the viscosity, which is important for the processability, of the solutions prepared therefrom is decreased by the addition of substances which contain a urea or guanidino group.

These effects can be further improved by separating out the fibrinogen polymers contained in the starting product, so that not only cryoprecipitates can be used as starting material, but also other fibrinogen precipitates. By this means, for example, more economic utilization of the costly cryoprecipitate is possible: thus, apart from F VIII concentrate, fibrinogen concentrates can also be prepared from a cryoprecipitate.

Thus, the invention relates to a solid fibrinogen formulation which contains a substance containing the urea or guanidine radical.

A guanidino compound is preferably added. Arginine is particularly suitable. These compounds are added in an amount such that their content in the formulation is 0.05 to 5 percent by weight.

The formulation is dried, preferably lyophilized.

In order further to improve the solubility of a fibrinogen formulation of this type, an aminoacid having a hydrophobic side chain, for example, L-leucine, or a water-soluble fatty acid, for example butyric acid, can be added to it in each case in an amount from 0.1 to 5 percent by weight.

An improvement in the rate of dissolution can be achieved by filling the gas space above the solid fibrinogen formulation with at least 20 percent by volume of carbon dioxide. The remainder of the gas atmosphere can be nitrogen, another inert gas or air.

Furthermore, the formulation can also contain albumin.

When used as a fibrin adhesive, factor XIII from human plasma or placenta can also be added to increase the resistance to tearing in the rat-skin tearing test described. A concentration between 40 and 60 U of factor XIII per ml of fibrinogen concentrate has been found to be optimal.

Addition of an inhibitor of fibrinolysis, for example aprotinin, can take place during dissolution of the fibrinogen concentrate: a fibrinogen concentrate containing 60 U of factor XIII, 1% of albumin and 8% of coagulable fibrinogen is, for example, dissolved with a solution of aprotinin having 1,000 kallikrein inhibitor units and then is induced to coagulate with a mixture of thrombin and calcium chloride. This mixture ensures a stable wound closure and also substantial protection against too rapid fibrinolysis.

The invention also relates to a process for the preparation of a fibrinogen formulation, which comprises maintaining a fibrinogen solution at a pH of 5 to 8 and at a temperature of $0°$ to $15°$ C. until the fibrinogen polymers have precipitated out, separating these off, adding a substance containing the urea or guanidine radical and drying.

The solid fibrinogen formulation according to the invention dissolves more rapidly and gives higher concentrations than those prepared according to the state of the art. Aqueous solutions can be obtained at room temperature which contain up to 14 g/100 ml of fibrinogen. If dissolution is carried out at $37°$ C., for example, even higher concentrations can be obtained.

Since, when fibrinogen solutions of this type are used as tissue adhesives, the tenacity of adhesion increases with the content of fibrinogen, greater tenacity is obtained with tissue adhesives derived from concentrates prepared according to the invention.

This can be demonstrated in the rat-skin tearing test: a circular piece of skin is removed from an anesthetized experimental animal using a punch. This piece of skin is painted with a mixture of one part by volume of the fibrinogen solution according to the invention and one part by volume of thrombin solution (400 NIH units/ml), then pressed onto the wound made by the punch, left there for 15 minutes and thereafter the tear-off weight is determined.

TABLE

Dependency of the tenacity of adhesion on the fibrinogen concentration in the rat-skin tearing test

| Fibrinogen concentration, % | Tear-off weight in g; mean value of 10 tests | |
|---|---|---|
| | $\overline{X}$ | s |
| 12 | 206 | 39 |
| 8 | 132 | 36 |
| 4 | 113 | 51 |
| 0 (control) | 16 | 12 |

A further advantage of the fibrinogen concentrates prepared in the manner described is their stability after reconstitution. Since impurities of prothrombin factors and plasminogen are normally present in cryoprecipitates, the stability of cryoprecipitate solutions at room temperature is limited to 2 to 4 hours. Fibrinogen concentrates prepared according to the following Example 2 are, in contrast, stable at room temperature for a working day.

The following examples are intended to illustrate the invention.

EXAMPLE 1

Preparation of a fibrinogen concentrate from cryoprecipitate

A cryoprecipitate from citrated plasma was dissolved in a 0.01M Na citrate solution of pH 8.5 containing 1% (w:v) of arginine at 37° C. The undissolved fraction was removed by centrifugation in an ultracentrifuge (Beckman J 21-B, Rotor JA 14) (45 minutes, 15,000 rpm) and discarded.

After adjustment of the fibrinogen concentration to about 5% (w:v) protein, the pH was maintained between 7.0 and 9.0. After sterilization by filtration, filling out and flooding the container with 100% by volume of carbon dioxide, a lyophilizate was obtained, from which aqueous fibrinogen solutions containing up to 12% (w:v) of fibrinogen could be prepared at room temperature.

EXAMPLE 2

Preparation of a fibrinogen concentrate from a fibrinogen precipitate 6 kg of a fibrinogen precipitate, which had been precipitated from a cryoprecipitate from citrated plasma using a 2M glycine solution, were washed with 35 liters of buffer (0.15M NaCl, 0.01M citrate and 1M glycine) of pH 8.0 and the supernatent was removed by centrifugation. The residue was dissolved in 9 liters of 0.01M citrate and 0.15M NaCl of pH 8.0 at 37° C. The pH must be below 8. The solution was allowed to stand overnight at 8° to 10° C. and the precipitate was removed by centrifugation at 8° C.

The supernatant was dialyzed twice against a buffer of pH 8, which was composed of 0.05M NaCl, 0.005M citrate, 1 g/100 ml of L-arginine and 0.8 g/100 ml of L-leucine.

For use as a fibrin adhesive, after dialysis, 60 U of factor XIII per ml and 10 mg of human albumin per ml are added.

The solution was sterilized by filtration, lyophilized and the product was covered with a mixture of 50% by volume of carbon dioxide and 50% by volume of nitrogen.

For intravenous use, the lyophilizates can be dissolved in the concentration for filling out of about 2–3% of fibrinogen; for use as fibrin adhesives, they are dissolved in correspondingly less solvent, so that concentrations between 8 and 10% of fibrinogen are obtained.

We claim:

1. A lyophilized fibrinogen formulation consisting essentially of fibrinogen and from 0.05 to 5 percent by weight of a substance selected from the group consisting of arginine, creatine, creatinine, glycocyamine, urea and citrulline, said substance enabling the fibrinogen to be readily dissolved in an aqueous solution to a concentration of 2 to 14 percent by weight.

2. A formulation as claimed in claim 1 which further comprises at least 0.1 to 5 percent by weight of either an amino acid having a hydrophobic side chain or a water-soluble fatty acid.

3. The lyophilized formulation of claim 1 consisting essentially of fibrinogen and arginine.

4. A formulation as claimed in claim 3 which further comprises at least 0.1 to 5 percent by weight of either an amino acid having a hydrophobic side chain or a water-soluble fatty acid.

5. A formulation as claimed in one of claims 2, 3 or 4 which further comprises factor XIII and aprotinin.

* * * * *